United States Patent [19]
Hammerstedt et al.

[11] Patent Number: 6,065,294
[45] Date of Patent: May 23, 2000

[54] CASSETTE DEVICE AND SYSTEM TO FACILITATE CRYOPRESERVATION

[75] Inventors: Roy H. Hammerstedt, Boalsburg; Wesley Glebe, State College, both of Pa.; Rupert P. Amann, Fort Collins, Colo.

[73] Assignee: BioPore, Inc., State College, Pa.

[21] Appl. No.: 09/136,552

[22] Filed: Aug. 19, 1998

Related U.S. Application Data

[60] Provisional application No. 60/056,608, Aug. 20, 1997.

[51] Int. Cl.[7] .................................................. F25B 21/02
[52] U.S. Cl. .................................. 62/3.3; 62/371; 62/62; 422/65
[58] Field of Search ................. 62/3.3, 371, 62, 62/64, 336, 3; 422/65

[56] References Cited

U.S. PATENT DOCUMENTS

| | | | |
|---|---|---|---|
| 3,743,104 | 7/1973 | Peterson | 211/60 |
| 4,256,697 | 3/1981 | Baldwin | 422/104 |
| 4,799,358 | 1/1989 | Knopf et al. | 62/3 |
| 5,026,342 | 6/1991 | Hammerstedt et al. | 600/35 |
| 5,061,630 | 10/1991 | Knopf et al. | 435/290 |
| 5,240,857 | 8/1993 | Lahetkangas | 435/316 |
| 5,261,870 | 11/1993 | Hammerstedt et al. | 600/35 |
| 5,446,263 | 8/1995 | Eigen et al. | 219/521 |
| 5,459,300 | 10/1995 | Kasman | 219/433 |
| 5,508,197 | 4/1996 | Hansen et al. | 435/285.1 |
| 5,609,826 | 3/1997 | Cargill et al. | 422/99 |
| 5,616,301 | 4/1997 | Moser et al. | 422/104 |
| 5,670,120 | 9/1997 | Degenhardt et al. | 422/104 |
| 5,736,106 | 4/1998 | Ishiguro et al. | 422/131 |
| 5,779,981 | 7/1998 | Danssaert et al. | 422/99 |

*Primary Examiner*—Henry Bennett
*Assistant Examiner*—Chen-Wen Jiang
*Attorney, Agent, or Firm*—Webb Ziesenheim Logsdon Orkin & Hanson, P.C.

[57] ABSTRACT

A long rectangular slotted-sheath construct generally referred to as a "cassette," functions both in the positioning of and the treating of the individual, cell-containing primary units held therein. The invention also embraces a cooling and thawing system within which primary containers of cells, with or without a surrounding cassette, may be cooled, stored and rewarmed.

13 Claims, 6 Drawing Sheets

CASSETTE DEVICE AND SYSTEM TO FACILITATE CRYOPRESERVATION

RELATED APPLICATIONS

This application is based on priority Provisional Application Ser. No. 60/056,608, of which the following specification is a Continuation-in-Part.

FIELD OF THE INVENTION

The present invention relates to cassettes and other mechanical configurations to facilitate the cryopreservation and thawing of cells or tissues.

BACKGROUND OF THE INVENTION

Cryopreservation is a procedure for preparation of a suspension of cells, or a group of cells such as an embryo, for storage. The procedure normally incorporates adding cryoprotectants to the cells to be preserved, cooling of the suspended cells, long-term storage of the cell suspension at temperatures below about $-80°$ C., warming of the cells to normal cell temperatures, and removal of cryoprotectant from the cells. Cryopreservation of sperm or other cells from common mammals is a deceptively simple-appearing process which succeeds despite certain serious obstacles. This success depends on the use of one or more cryoprotectants in the context of certain procedural parameters.

Overall cryopreservation procedures generally thus include: preparation of a suspension of cells for low-temperature storage by incorporation of cryoprotectants, and placement of individual units into vials or "straws"; cooling (sometimes called "freezing") at an appropriate rate; long-term storage of the suspension of cells at a temperature lower than $-80°$ C. and often between $-180°$ C. and $-196°$ C.; distribution at low temperature to intermediaries or users; warming (sometimes called "thawing") at an appropriate rate to the normal cellular temperature; and controlled removal of cryoprotectant plus any other medium or other adjustments needed to render the cells ready for in vivo use. The goal is not just to keep cells alive (viable), but to optimize retention of all cellular attributes such as normal life span, oxygen-carrying potential (especially in the case of erythrocytes) and fertilizing potential (in the case of spermatozoa or oocytes), for which the cells are being preserved in the first place.

Notwithstanding cell type, species of origin or the various protocols used, prior art cryopreservation protocols traditionally result in about 30% mortality (or worse) of cells being preserved. Many cells traditionally did not survive the cooling and rewarming, and those which did suffered further damage during the removal of the intracellular cryoprotectant. Damage can result from any or all of improper rates of temperature changes during cooling and rewarming; formation of ice crystals; reduction in temperature per se; toxicity due to high concentrations of solutes within and around the cells; the nature and concentration of the cryoprotectant(s) used; rates of addition and removal of cryoprotectants from within the cells; and other lesser known but empirically evident factors.

Depending on the number of cells required for a functional "unit" after thawing, cells are traditionally packaged in individual "units" using glass ampules, plastic vials, plastic straws, or appropriately sized plastic bags. These packages all require removal of the cell suspension from the primary container before slow removal of cryoprotectant. Slow removal of cryoprotectant conventionally is achieved by dilution followed by centrifugation to re-concentrate the cell suspension or by washing cells via counter-flow centrifugation. Alternatively, technology disclosed in U.S. Pat. Nos. 5,026,342 and 5,261,870, incorporated herein by reference, allow removal of cryoprotectant from a primary container while cells of that individual unit remain therein; such primary containers are formed with walls or membranes having plugged pores which can be opened at a predetermined time to retain cells within the container but to allow exchange of fluid and molecules through the pores.

It is a common practice in the cryopreservation of cells: (1) to seal the primary container (such as a vial or straw) after it is filled with cells and before freezing; (2) to cool (sometimes called freezing) individual units at an appropriate rate to $-196°$ C.; (3) to group the primary containers in storage "boxes" or "goblets and canes" after which they are held at low storage temperatures such as $-196°$ C.; and (3) removing primary containers from this storage box or cane before warming (sometimes called thawing) the contents of the primary container by procedures known to those skilled in the art. U.S. Pat. No. 3,743,104 discloses a system in which straws containing semen are sealed by procedures known in the art and then placed into a "special cane" in which the metal has been formed to hold two groups of 4–10 straws during subsequent freezing and storage, with the straws being removed individually from the special cane prior to thawing. Use of a special cane in this way is more labor intensive than is optimal.

Conventional procedures for preservation of many types of cells have involved controlled cooling from room temperature of $4°$ C. to $-80$ or $-100°$ C., followed by plunging the containers of cells into liquid nitrogen at $-196°$ C. or storage in vapor above liquid nitrogen. This reflects recognition that there are complex interactions among rate of cooling, concentrations of cryoprotectants and other solutes, temperature or spontaneous or planned "seeding," and other factors. It is equally well known that there is an interaction between cooling and warming rates but there has been no practical method to achieve a defined warming rate from at or below $-40°$ C. to $4°$ C. Warming rate has been controlled passively on the basis of the surrounding medium (i.e., ambient air, ice water, $37°$ C. water) rather than what is desirable from the standpoint of optimization of cellular attributes. Also, when water is used as a warming liquid, there is concern that water might leak into the primary package containing the cells and kill or seriously damage them.

A need thus remains for a mechanical means to arrange, store and transport individual units of cells intended for low temperature storage, which means provides positioning for the units from the time the initial cellular suspension is charged therein throughout many subsequent steps including but not limited to cooling and storage.

SUMMARY OF THE INVENTION

In order to meet this need, the present invention is a long rectangular slotted-sheath construct generally referred to as a "cassette," which functions both in the positioning of and the treating of the individual, cell-containing primary units held therein. The invention also embraces a cooling and rewarming (thawing) system within which primary containers of cells, with or without a surrounding cassette, may be cooled, stored and rewarmed from cryogenic temperatures to warmer than freezing temperature.

DETAILED DESCRIPTION OF THE INVENTION

The present invention is a long rectangular slotted-sheath construct generally referred to as a "cassette," which functions both in the positioning of cell-containing primary containers held therein for filling, sealing, and storage and also treating said primary containers during cooling and warming. The invention also embraces a warming (thawing) system within which primary containers of cells, with or without a surrounding cassette, may be rewarmed at a selected rate.

As a general practice, individual primary containers for cell suspensions such as spermatozoa and erythrocytes are prepared according to U.S. Pat. Nos. 5,026,342 and 5,261,870, as herein incorporated above. These containers are optimally rectangular containers having two major faces fabricated from a plugged-pore membrane as described therein, which have proved particularly useful for the cryopreservation and post-thaw removal of cryoprotectant of rooster sperm. Large-scale use of this approach has been hampered, however, by the need to handle each primary container as an individual unit during filling, sealing, cooling, transfer into and removal from a cryogenic tank for storage at −196° C., warming, and post-thaw deglycerolation. The present cassette therefore was designed not only to hold such primary containers in a useful array, but to contain features which would facilitate completion of certain steps. The primary containers therefore remain in the cassette until immediately before cryoprotectant removal.

Figure 1:
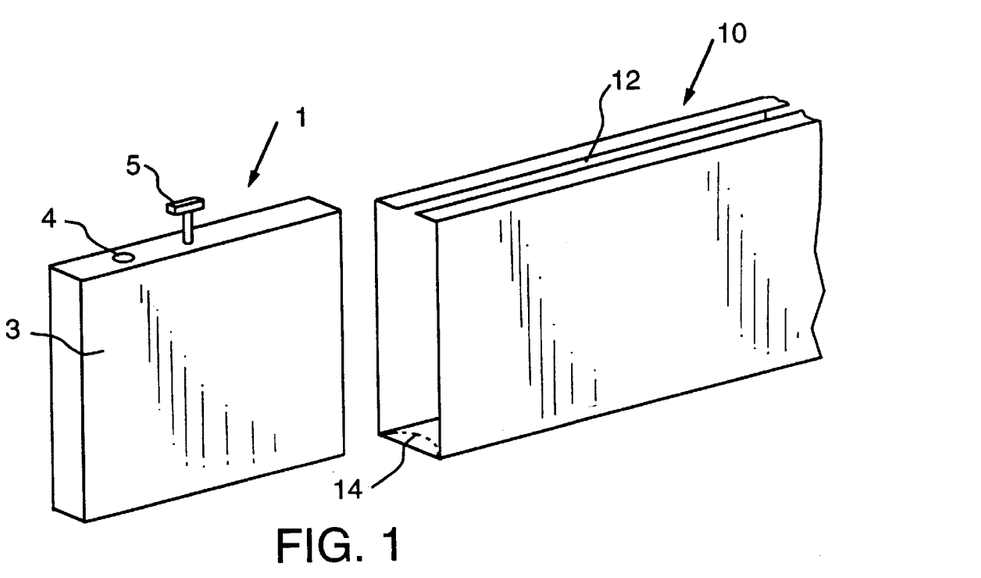
FIG. 1 is a perspective view of a cassette 10 according to the invention, adapted to receive a primary container 1 therein.

The general nature of a cassette according to the present invention is shown in FIG. 1. Dimensions may be scaled to accommodate 10 primary containers of 1 ml capacity each, but dimensions play little part in the concept of the present invention with one caveat described below. Cassettes as shown may be made from aluminum or other metal, but plastic, polymer or composite could be used. The important elements of the cassette have to do with the following features: (a) snug fit of the primary containers therein, in a position which allows them to be filled with a cell suspension and sealed; (b) retention of primary containers during subsequent freezing and storage; (c) necessary degree of effective heat transfer ability; and (d) appropriate size and shape for incorporation in standard cryopreservation equipment in general use for freezing and storing cell suspensions. Optimally, therefore, the device of FIG. 1 is fabricated of aluminum, having a gauge between about 0.01 and 0.10 inches in thickness, in the shape as shown and with dimensions of the longest face not exceeding about 11 inches.

Referring now to FIG. 1, the present cassette is a long rectangular slotted-sheath receptacle 10 having a slotted aperture 12 therein. The slotted sheath structure, apart from containing a slot in its uppermost face, is a rectilinear four-walled construct. Optionally, however, the bottom face may be fabricated as an optional concave surface 14, to provide a spring-loading function better to hold the primary container 1 after it is in place (as discussed below).

Figure 2:
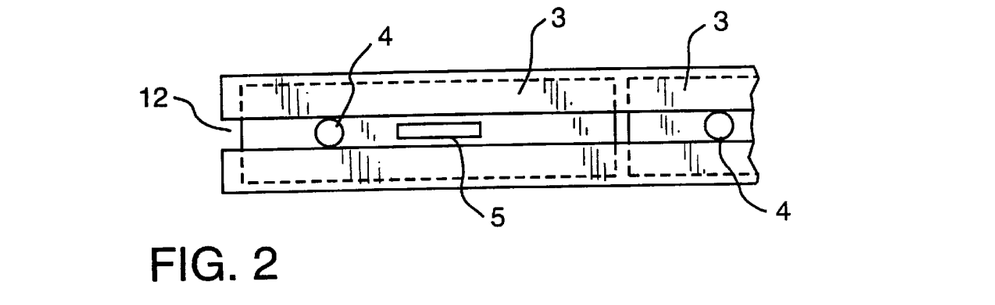
FIG. 2 is a plan view of the primary container 1 of FIG. 1 in place within the cassette 10 of FIG. 1.

The cassette is adapted to receive, by insertion via its open end, a primary container 1 comprising a generally rectangular, hollow construct having a porous surface 3 on two opposing sides thereof and an aperture 4 in the upper surface thereof. The porous surface contains pores which are initially filled with an erodible or otherwise removable pore plugging substance as further described in U.S. Pat. Nos. 5,026,342 and 5,261,870, heretofore incorporated herein by reference. The primary container 1 also contains a channel guide 5 atop its upper surface, which as shown is a T-shaped appendage but which may comprise any protrusion of the upper surface of the primary container 1. The aperture 4 is a filling hole for the primary container 1, through which cells in suspension may be charged to the primary container 1 for cryopreservation and storage. After placing a cell suspension into primary container 1, said aperture 4 is sealed, with UV glue or other methods known to those skilled in the art, by working through slotted aperture 12. The cassette, with primary container therein, then can be cooled to −196° C. and stored, by procedures known to those skilled in the art.

Regardless of the primary package used to cryopreserve cells, there is a need to warm (thaw) the cells in a repeatable manner at a controlled rate from below −40° C. to 5° C. or 37° C. Traditionally, thawing is by immersion of a primary container in a relatively large volume of water at 4° C. or 37° C. or other temperature, which in turn means that the thawing rate is dictated by the water temperature. Alternatively, in a research setting, a computer-controlled, liquid nitrogen vapor freezing machine known in the art can be run in "reverse mode" to warm containers at a controlled rate. To meet the need for a low-cost device which provides an operator-defined warming rate and accommodates primary containers of various sizes and shapes (not to mention containers positioned within the present cassette), a novel device was developed to include a rectangular, insulated container with a control unit not integral to the thermal block. As described below, it provides for low cost, portability, ease of use, relatively fool-proof use via automation, operation using temperatures between −40° C. to 37° C., and adaptability to warming primary containers of varying size, shape and number.

Figure 3:
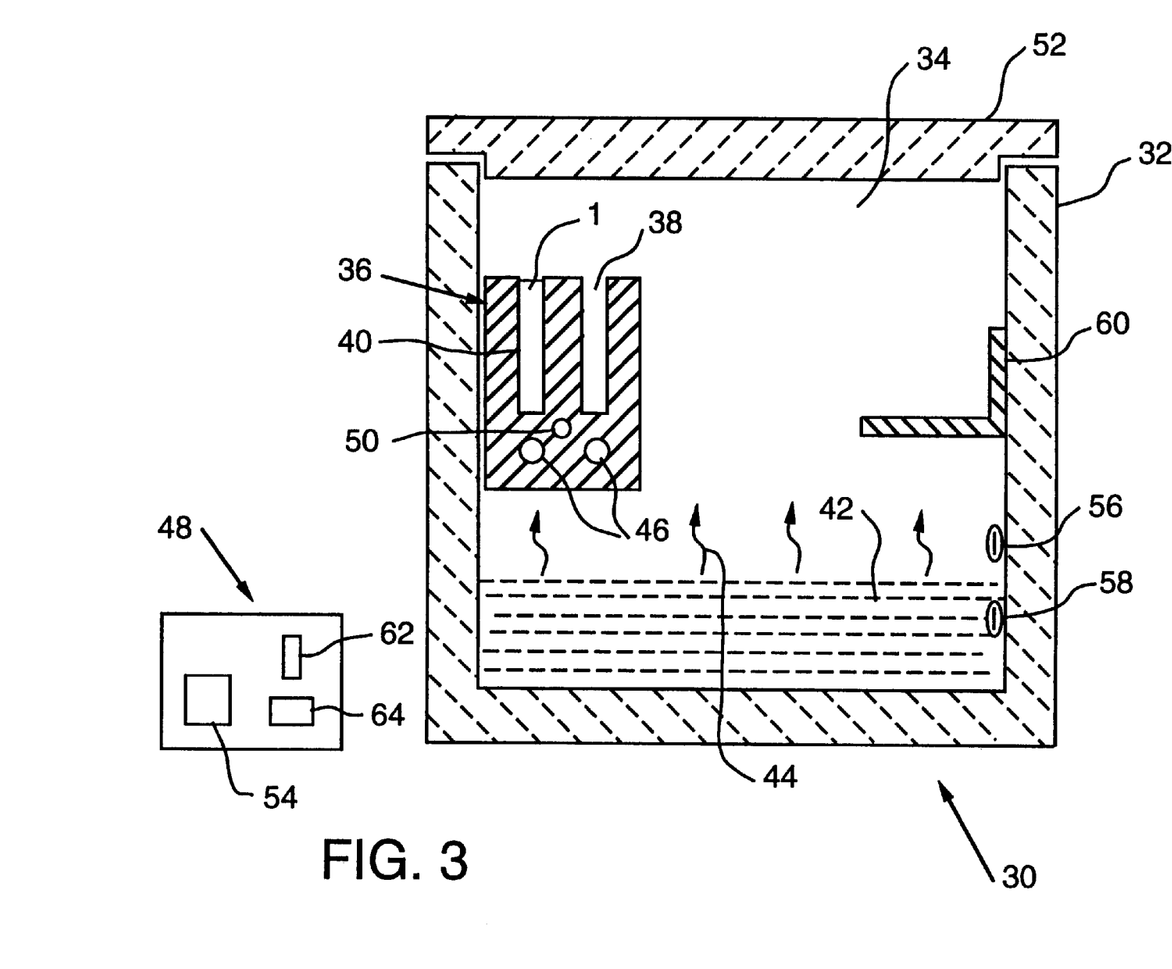
FIG. 3 is a side sectional view of a rewarming device 30 according to the invention.

This further novel device is shown in FIG. 3. FIG. 3 portrays a container 30 having insulated walls 32 and lid 52, said insulated walls 32 defining a cavity 34 containing a thermal block 36 formed from aluminum or other material, said thermal block 36 having at least one recessed area 38 therein to accommodate either at least one primary container 1 containing cryopreserved cells or at least one cassette 40 in turn containing at least one primary container 1. The cavity 34 also contains coolant fluid 42, which is typically liquid nitrogen or liquid carbon dioxide or a solvent known to those skilled in the art (i.e., isopropyl alcohol) cooled by solid carbon dioxide. The cavity 34 also contains vapor 44 above the coolant fluid. The thermal block 36 further incorporates at least one resistance heater 46 appropriately sized and connected to a control box 48 providing current to the heater 46 as needed to maintain the desired temperature. Also within the thermal block 36 is a temperature sensor 50, such as a thermistor, also connected to the control box 48.

Within the control box 48 are a circuit board 54 connected to the resistance heaters 46, a power source and the temperature sensor 50, in turn, together with various indicator lights and switches. Connection between the thermal block 36 and the circuit board 54 may be by means known in the art. Sensors to detect whether the level of coolant 42 within the container 30 is too high or too low appear as sensors 56 and 58, respectively, which feed in turn into the microprocessor 64. An optional shelf 60 may be positioned within the cavity 34 to provide a staging area for a primary container 1 or cassette 40 prior to placement within the recessed area 38 within the thermal block 36.

Further with respect to FIG. 3, the circuit board 54 further contains a microprocessor 64 and a temperature electronics unit 62 together with power control switches, other control switches and indicator lights (not shown). Each of these individual elements uses approaches, circuits and components as are known in the art. The microprocessor contains, as variable data entered earlier in memory, details of the automation program, namely: initial temperature; interval between initiating a "run" and start of warming; warming rates in 1 or more segments, defined on the basis of an elapsed time and desired temperature at the end of that time, assuming a linear rate for each segment of the warming curve; desired final hold temperature; and when signals should be sent to indicator lights displaying the ongoing warming process. The temperature electronics unit 62 energizes the thermistor 50, receives and processes the signal therefrom, and provides a series of temperature readings to the microprocessor 64. The power control circuit is intermittently energized, as a deviation between desired and actual temperature is detected by the microprocessor, and provides current to the resistance heater for a predetermined interval. Incorporation of two or more temperature-power circuits may be desirable to provide rapid-coarse adjustment of temperature and, alternatively, low-fine adjustment of temperature. The control switches not shown in FIG. 3 may include, without limitation, an "on-off" switch, a "seek initial low starting temperature" switch, and a "start the warming process" switch. The indicator lights, when used, may coordinate with the microprocessor 64 to indicate to the user the status of the instrument. Status can include, without limitation, on/standby, cooling fluid level within specified range, insufficient cooling fluid, excess cooling fluid, ready at predefined start temperature, warming at desired rate, temperature outside control limits, or holding at final temperature, as examples. There also might be audible as well as visual signals in the disclosed system.

In operation, the thermal block 36 and the optional shelf 60 are positioned within the cavity 34, and an appropriate volume of coolant 42 is charged to the cavity 34. Before the lid 52 is positioned thereover, containers of cells to be preserved may be placed temporarily on the shelf 60. The power circuit is activated, and the control switch turns on the initialization program causing the unit to adjust to the initial (low) temperature. The initial temperature is achieved within the thermal block 36 by balancing the action of the coolant 42 with the action of the resistance heater, microprocessor, and aforementioned coordinated control devices. The liquid level sensors 56 and 58 alert the operator if the level of coolant is inappropriate. When the designated initial temperature is achieved, a signal is activated and the containers of cells to be warmed (in primary containers 1 in turn optionally residing in cassettes 40) are transferred into their respective recessed area(s) 38 within the thermal block 36, with removal and replacement of the lid 52 as needed. The switch initiating the warming program is then activated.

For a predetermined interval, the thermal block 36 is held at the initial temperature and then, automatically, warming is initiated at the desired rate. Frequent sampling of temperature within the thermal block 36, via the temperature sensor 50, with comparison of actual and desired temperatures and concomitant on/off switching of the resistance heaters 46, gradually increases temperature and warms the thawing cells. Indicators monitor the rewarming protocol, and the primary container(s) 1 and/or cassette(s) 40 may then be removed from the cavity 34 after removing the lid 52.

Figure 4:
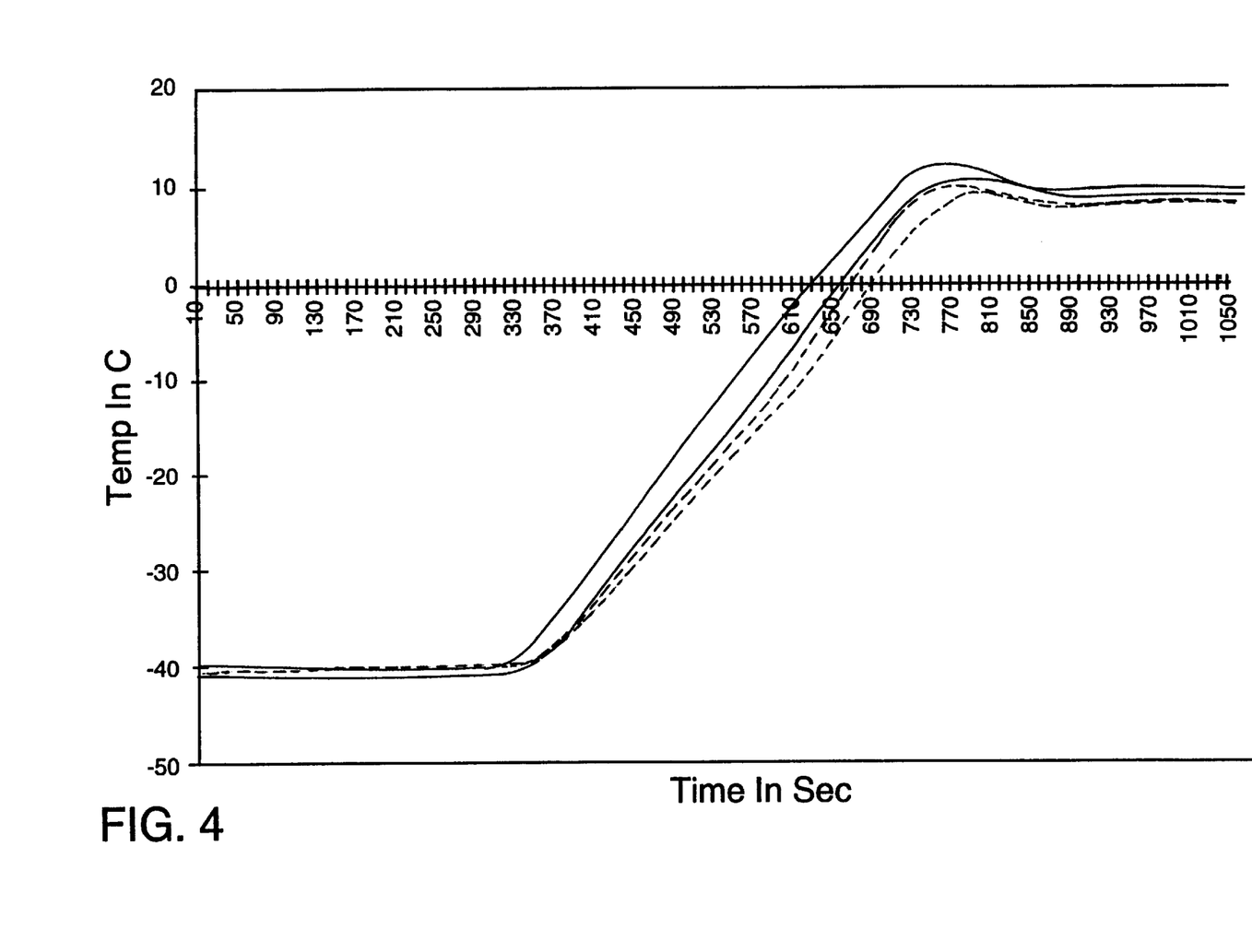
FIG. 4 is a graphic representation of a typical warming curve within the frozen cell suspension within a primary container 1, generated by the sensors and heaters of the device 30 of FIG. 3.

Typical warming curves are shown in FIG. 4. The solid line shows the programmed warming rate as reflected by temperature measured by the temperature sensor 50 and the other lines show the warming rates as monitored by a micro-thermocouple placed into primary containers located in two separate cassettes. Other samples of rooster sperm were processed, placed into primary containers, prepositioned within the present cassette, sealed therein, frozen and stored at $-196°$ C., and thawed by placing the cassettes in the thawing device of FIG. 3. When used for the artificial insemination of hens, greater than 50% of all eggs laid contained a live embryo.

Figure 5:
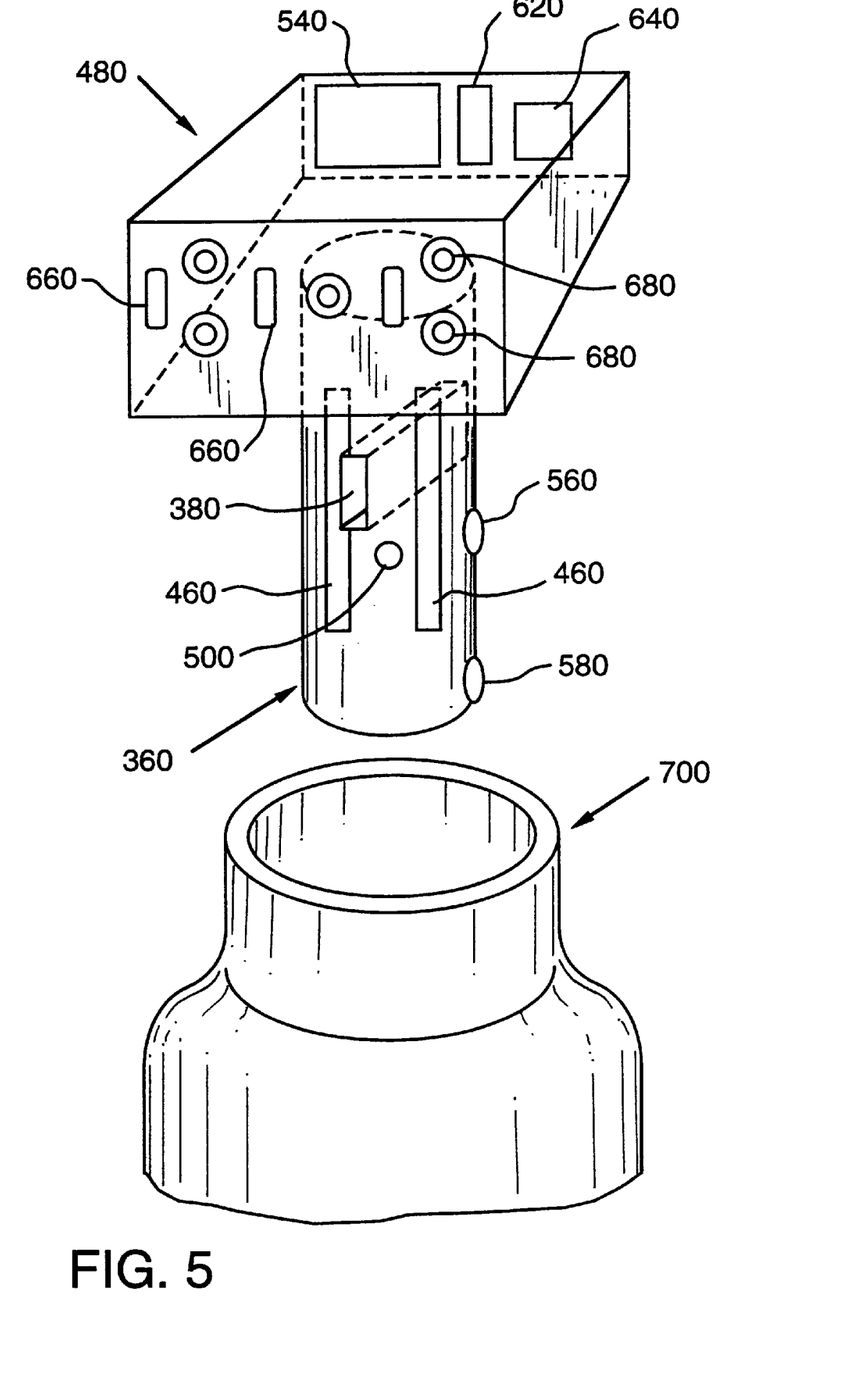
FIG. 5 is a side sectional view of an alternate embodiment of a cooling and rewarming device according to the present invention.

An alternative embodiment of a system for the controlled-rate thawing of cells stored in primary container(s) within cassette(s) is shown in FIG. 5, in which the individual components of FIG. 3 appear in a different orientation and arrangement. In FIG. 5, the control box 480 is directly, physically connected to the thermal block 360. Each structure in FIG. 5 which is analogous to a structure in FIG. 3 is designated by the same reference numeral plus a trailing zero, for easy reference. For example, the temperature sensor 50 in FIG. 3 appears as the temperature sensor 500 in FIG. 5, and so on. Unlike FIG. 3, however, switches 660 and indicator lights 680 are illustrated. Coolant (not shown) is charged to a vacuum bottle 700. As is apparent from FIG. 5, primary containers with or without their enveloping cassettes are slidably mounted into the recessed area 380.

Figure 6:
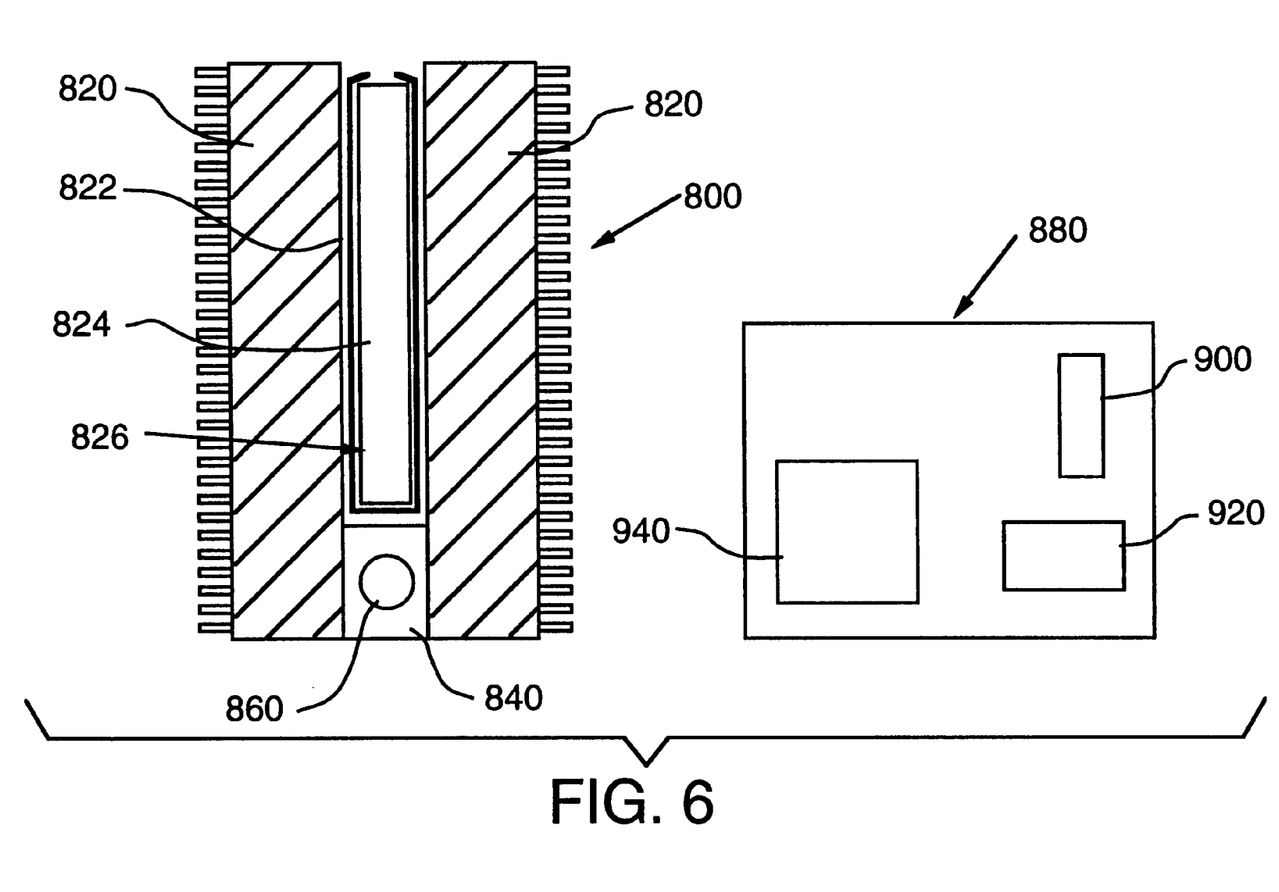
FIG. 6 is a side sectional view of an alternative embodiment of the thermal block of a rewarming device and control box according to the present invention.
Figure 7:
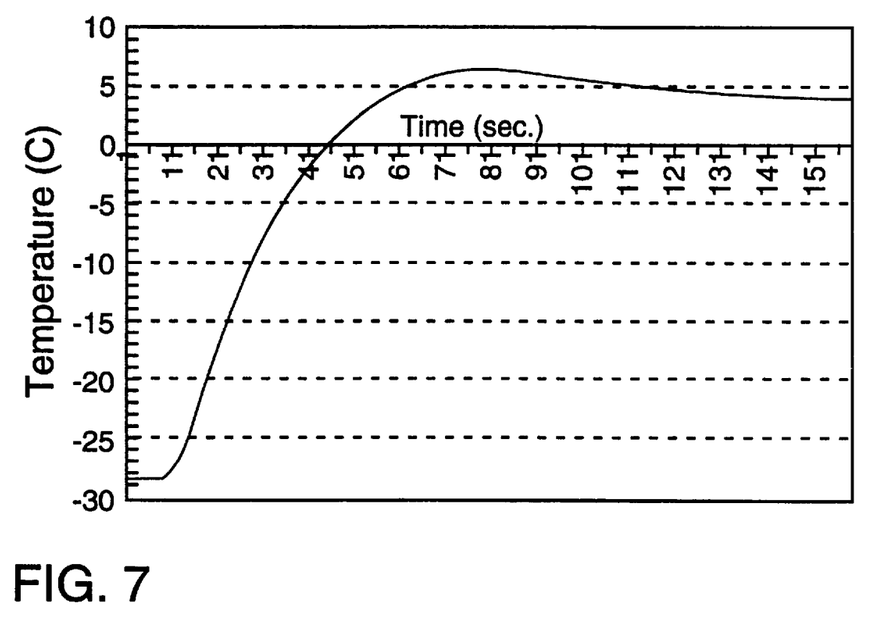
FIG. 7 is a graphic representation of a typical warming curve within the frozen cell suspension within a primary container 1, generated by the sensors of the device 30 of FIG. 6.

In a further variation of the present invention as shown in FIG. 6, thermal block 800 incorporates thermoelectric heat pumps 820 in addition to the recess 822, the primary container 824 housed within its cassette 826. A small spacer 840 separates the thermoelectric heat pumps 820, forms the bottom of the recess 822, and accommodates the temperature sensor 860. In this embodiment, many of the components shown in FIG. 3 are unnecessary (e.g., insulated walls 32, liquid nitrogen 42, or sensors 56 and 58). As in the previously described embodiments of the invention, the temperature sensor 860 intercommunicates with a controller 880 including a temperature profiler 900, a proportional integral differential control unit 920, and a power supply 940. Placement of the primary cell container or cassette into the recess(es) allows temperature equilibration with the heat pump removing or adding heat as needed to maintain the selected starting temperature. Initiation of the warming cycle and feedback control to provide the desired warming rate are essentially as detailed in conjunction with the description of FIG. 3. A typical warming curve obtained with the device of FIG. 6 is shown in FIG. 7, with warming in this example from near $-29°$ C. to $+5°$ C. in less than 1 minute, with subsequent holding at $5°$ C. Note that the rate of temperature rise and degree of overshoot near the desired final temperature can be controlled with high precision via use of the thermoelectric heat pumps and the proportional integral differential control unit, known to those in the art. As in the alternate embodiments, the recess 822 can be dimensioned to accept primary containers of different sizes or shapes, either as single containers or multiple containers with or without cassettes according to the present invention.

Although the invention has been described with particularity heretofore, with reference to particular materials and structures, the invention is only to be limited insofar as is set forth in the accompanying claims. For example, the "cavity" and "recess" structures described hereinabove both perform a sleeve function, and the terms cavity and recess should thus be considered interchangeable for the purpose of the following claims.

We claim:

1. A processing system to warm at least one primary container containing a suspension of cryopreserved cells, comprising:

a thermal block, the temperature of which can be regulated, positioned adjacent to a heat exchange material, said thermal block having at least one cavity therein, said cavity further comprising a receptacle adapted to accept a primary container, said primary container containing pores which are initially plugged.

2. The processing system according to claim 1 wherein said cavity further receives a cassette therein, said cassette further comprising an elongated rectangular construct having a continuous slot along the upper face thereof, said cassette being adapted to receive said primary container.

3. The processing system according to claim 1 wherein said thermal block contains a temperature sensor.

4. The processing system according to claim 1 wherein said thermal block contains warming means therein.

5. The processing system according to claim 1 wherein said thermal block is intercommunicatively connected to a control means.

6. The processing system according to claim 1 wherein said heat exchange material is a coolant.

7. The processing system according to claim 1 wherein said cavity and heat exchange material are formed by or incorporate one or more thermoelectric heat pumps.

8. The processing system according to claim 1 wherein said heat exchange material is liquid nitrogen.

9. A cassette for use in conjunction with the cooling and warming method of claim 2, said cassette comprising an elongated rectangular construct having a continuous slot along the upper face thereof and at least one open end perpendicular to said slot.

10. The cassette according to claim 9 wherein said elongated rectangular construct is metal.

11. The cassette according to claim 9 wherein said elongated rectangular construct is sheet aluminum.

12. The cassette according to claim 9 wherein said elongated rectangular construct is dimensioned to receive at least one primary container containing cells to be cryopreserved.

13. The cassette according to claim 12 wherein said elongated rectangular construct has a concave face on the bottom surface thereof.

* * * * *